US010086017B2

(12) United States Patent
Chakravarthy et al.

(10) Patent No.: US 10,086,017 B2
(45) Date of Patent: Oct. 2, 2018

(54) WOUND DRESSING CONTAINING POLYSACCHARIDES

(71) Applicant: MEDLINE INDUSTRIES, INC., Mundelein, IL (US)

(72) Inventors: Debashish Chakravarthy, Vernon Hills, IL (US); Andrew J. Ford, Libertyville, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 14/031,736

(22) Filed: Sep. 19, 2013

(65) Prior Publication Data

US 2015/0079196 A1    Mar. 19, 2015

(51) Int. Cl.
*A61K 31/715* (2006.01)
*A61K 35/644* (2015.01)
*A61K 36/899* (2006.01)
*A61F 13/00* (2006.01)

(52) U.S. Cl.
CPC ...... *A61K 35/644* (2013.01); *A61F 13/00012* (2013.01); *A61K 31/715* (2013.01); *A61K 36/899* (2013.01)

(58) Field of Classification Search
None
See application file for complete search history.

(56) References Cited

U.S. PATENT DOCUMENTS

| | | |
|---|---|---|
| 3,767,784 A | 10/1973 | Gluck |
| 4,401,651 A | 8/1983 | Knutson |
| 4,838,253 A | 6/1989 | Brassington |
| 4,844,898 A | 7/1989 | Komori |
| 4,921,704 A | 5/1990 | Fabo |
| 4,995,382 A | 2/1991 | Lang |
| 5,147,338 A | 9/1992 | Lang |
| 5,298,015 A | 3/1994 | Komatsuzaki |
| 5,340,363 A | 8/1994 | Fabo |
| 5,352,508 A | 10/1994 | Cheong |
| 5,476,443 A | 12/1995 | Cartmell |
| 5,540,922 A | 7/1996 | Fabo |
| 5,556,375 A | 9/1996 | Ewall |
| 5,591,447 A | 1/1997 | Jensen |
| 5,635,201 A | 6/1997 | Fabo |
| 5,674,523 A | 10/1997 | Cartmell |
| 5,973,221 A | 10/1999 | Collyer |
| 5,980,875 A | 11/1999 | Mousa |
| 6,011,194 A | 1/2000 | Buglino |
| 6,051,747 A | 4/2000 | Lindqvist |
| 6,207,875 B1 | 3/2001 | Lindqvist |
| 6,479,724 B1 | 11/2002 | Areskoug |
| 6,552,244 B1 | 4/2003 | Jacques |
| 6,566,577 B1 | 5/2003 | Addison |
| 6,770,793 B2 | 8/2004 | Brooks |
| 7,154,017 B2 | 12/2006 | Sigurjonsson |
| 7,161,056 B2 | 1/2007 | Gudnason |
| 7,220,889 B2 | 5/2007 | Sigurjonsson |
| 7,223,899 B2 | 5/2007 | Sigurjonsson |
| 7,227,050 B2 | 6/2007 | Sigurjonsson |
| 7,230,154 B2 | 6/2007 | Sigurjonsson |
| 7,304,202 B2 | 12/2007 | Sigurjonsson |
| 7,381,860 B2 | 6/2008 | Gudnason |
| 7,396,975 B2 | 7/2008 | Sigurjonsson |
| 7,402,721 B2 | 7/2008 | Sigurjonsson |
| 7,411,109 B2 | 8/2008 | Sigurjonsson |
| 7,423,193 B2 | 9/2008 | Sigurjonsson |
| 7,459,598 B2 | 12/2008 | Sigurjonsson |
| 7,468,471 B2 | 12/2008 | Sigurjonsson |
| 7,470,830 B2 | 12/2008 | Sigurjonsson |
| 7,488,864 B2 | 2/2009 | Sigurjonsson |
| 7,507,870 B2 | 3/2009 | Nielsen |
| 7,531,711 B2 | 5/2009 | Sigurjonsson |
| 7,619,130 B2 | 11/2009 | Nielsen |
| 7,696,400 B2 | 4/2010 | Sigurjonsson |
| 7,745,682 B2 | 6/2010 | Sigurjonsson |
| 7,842,848 B2 | 11/2010 | Janusson |
| 7,910,793 B2 | 5/2011 | Sigurjonsson |
| RE42,755 E | 9/2011 | Molan |
| 8,026,406 B2 | 9/2011 | Janusson |
| 8,093,445 B2 | 1/2012 | Sigurjonsson |
| 8,303,551 B2 | 11/2012 | Bray et al. |

(Continued)

FOREIGN PATENT DOCUMENTS

| | | |
|---|---|---|
| EP | 1325754 A1 | 7/2003 |
| WO | 2007045931 A2 | 4/2007 |
| WO | 2010010399 A2 | 1/2010 |

OTHER PUBLICATIONS

Gibson, D, et al, "MMPs Made Easy," Wounds International, Nov. 2009, p. 1-6, vol. 1, Issue 1, <<http://www.woundsinternational.com>>.

Notification of Transmittal of the International Search Report and the Written Opinion of the International Searching Authority, or the Declaration; International Patent Application No. PCT/US2014/053414, Medline Industries, Inc. (Chakravarthy, Debashish, et al); dated Dec. 3, 2014.

Notification of Transmittal of the International Search Report and the Written Opinion of the International Searching Authority, or the Declaration; International Patent Application No. PCT/US2014/053367, Medline Industries, Inc. (Chakravarthy, Debashish, et al); dated Dec. 2, 2014.

(Continued)

*Primary Examiner* — Terry A McKelvey
*Assistant Examiner* — Catheryne Chen
(74) *Attorney, Agent, or Firm* — Laubscher, Spendlove & Laubscher, P.C.

(57) ABSTRACT

A wound dressing makes use of polysaccharides, including the formation of a range of variable viscosity mixtures that use a solid polysaccharide such as medical grade cane sugar and a liquid polysaccharide such as honey, both of which have inherent beneficial properties for wound healing. The mixture is applied to an absorbent surface that is designed to absorb the mixed polysaccharide only partially.

10 Claims, 1 Drawing Sheet

(56) References Cited

U.S. PATENT DOCUMENTS

| | | |
|---|---|---|
| 8,512,770 B2 * | 8/2013 | Murray et al. ............... 424/757 |
| 2004/0054313 A1 | 3/2004 | Molan |
| 2004/0127826 A1 | 7/2004 | Caskey |
| 2005/0123591 A1 | 6/2005 | Meyer-Ingold et al. |
| 2007/0148214 A1 | 6/2007 | Cullen et al. |
| 2007/0148215 A1 | 6/2007 | Teslenko et al. |
| 2009/0148537 A1 | 6/2009 | Molan |

OTHER PUBLICATIONS

Supplementary European Search Report; European Patent Application No. EP14846650, Medline Industries, Inc. (Chakravarthy, Debashish, et al); dated Feb. 2, 2017.

Tovey, Frank, "Honey and sugar as dressing for wounds and ulcers," Feb. 1, 2000, XP055343285, web Feb. 7, 2017 <<https://www.researchgate.net/profile/Frank_Tovey/publication/12474821-Honey_and_sugar_as_dressing_for_wounds_and_ulcers/links/00b495232eb896ba86000000/Honey-and-sugar-as-dressing-for-wounds-and-ulcers.pdf>>.

Mathews, Karol, et al, "Wound management using sugar," Mar. 1, 2002, XP055343284, web Feb. 7, 2017 <<http://www.hungarovet.com/wp-content/uploads/2007/08/wound-management-using-sugar-2002.pdf>>.

Murandu, Moses, et al, "The use of granulated sugar to treat two pressure ulcers," Jan. 2, 2009, XP055343281, web Feb. 7, 2017 <<http://www.wintjournal.com/media/journals/_/248/files/the-use-of-granulated-sugar-to-treat-two-pressure-ulcers.pdf>>.

* cited by examiner

WOUND DRESSING CONTAINING POLYSACCHARIDES

FIELD OF THE INVENTION

The present invention relates to wound dressings that make use of polysaccharides, including the formation of a range of variable viscosity mixtures that use a solid polysaccharide such as medical grade cane sugar and a liquid polysaccharide such as honey, both of which have inherent beneficial properties for wound healing. The present invention further relates to the application of such mixtures on an absorbent surface that is designed to absorb the mixed polysaccharide only partially.

BACKGROUND

The use of polysaccharides or sugars in liquid form, such as honey, is known to be effective as a dressing for wounds, burns and skin ulcers. Benefits include that inflammation, swelling and pain are quickly reduced, that sloughing of necrotic tissue occurs without the need for debridement, and that growth of tissues to repair the wound is stimulated. As a consequence, healing occurs rapidly with minimal scarring, and often without any necessity for skin grafting. In addition, the use of solid polysaccharides or sugars such as cane sugar is also known. Cane sugar, which contains organic elements that are known to improve wound healing, is more concentrated in sugars than honey (honey contains more water than solid cane sugar).

It is well known that the ability of the sugar to debride and loosen necrotic tissue in the wound is driven by the effect of the exertion of osmotic pressure. This osmotic pressure is directly related to the concentration of sugars at the wound surface. Thus it would be beneficial for the sugar to be as pure as possible (and consequently unmixed with any other non sugar element) when it comes into contact with the wound in its role as a wound dressing. However, both liquid and solid polysaccharides, such as honey and cane sugar respectively, present usability issues for a wound dressing, and appropriate delivery systems are required.

Assuming that it should be almost pure sugar that comes in contact with the wound implies that this almost pure sugar should be in a form that is deliverable to a wound. In this context pure honey is not a suitable physical form. This is because pure honey flows too fast and, if applied to a wound, is more likely to spill out of it, than stay in it, and this effect is only minimally improved upon via the use of a secondary dressing such as gauze. Likewise, pure crystalline or powder sugar has usability issue. For example, powdered sugar is messy in terms of application in a wound and a secondary bandage is most certainly needed. Accordingly, it would be beneficial if some means were to be found to attach or adhere cane sugar to a secondary dressing but without the use of sugar diluting adhesives or any non-sugar matter.

In addition to the use of polysaccharides in the use of wound treatment, it is known that MMPs, which are part of the larger family of metalloproteinase enzymes, play an important part in wound healing. Although MMPs have the important role of breaking down proteins so that new tissue forms, when MMPs are present in a wound bed at too high a level, for too long a time, and in the wrong places, they begin to degrade proteins that are not their normal substrates. This can result in the unwanted destruction of beneficial proteins, such as growth factors, receptors and ECM proteins, that are essential for healing, and so ultimately impair healing. Substantial evidence has amassed that MMPs in general are highly elevated in wounds with delayed healing compared to acute healing wounds as discussed, for example, in Wounds International, "MMPs Made Easy" (Vol. 1, Issue 1, November 2009), which is incorporated herein by reference. The potentially damaging effects of these high levels is compounded by the fact that tissue inhibitors of metalloproteinases ("TIMPs") levels in chronic wounds are generally slightly lower than in acute wounds.

The most preferred methods of cleansing of necrotic tissue are often surgery, curettage or sharp debridement. However, it may not always be possible to use one of these methods on patients who are not suitable candidates for such fast and immediate debridement. Collagenase enzyme, a MMP, is itself sometimes used to promote debridement, thereby incurring the negative effects of MMPs in the wound. Accordingly, it is advantageous to provide an improved method of debridement that does not introduce MMPs into the wound.

U.S. Pat. No. RE42,755 to Molan describes a wound dressing incorporating a honey composition that is at least 50% honey and mixed with a gelling agent to render it formable, pliable, flexible and moldable. While this design does allow a liquid polysaccharide (honey) to be more conveniently delivered, the intimate mixing with the gelling agent causes the sugar concentration at the wound to be lowered than it would be without mixing with the gelling agent. In addition, Molan does not mention the MMP suppression effect of honey.

U.S. Pat. No. 4,844,898 to Komori, U.S. Pat. No. 3,767,784 to Gluck, and U.S. Pat. No. 4,401,651 to Knutson also discuss polysaccharide compositions for use with wound dressings. Each of these references fails to recognize that the efficacy of polysaccharides is driven by the exertion of osmotic pressure. This osmotic pressure effect causes wound exudates to flood in from deep within tissue into the wound site, dissolving necrotic tissue and cleansing the wound. Accordingly, these references do not teach that the dilution of the polysaccharide by non-active ingredients, such as viscosity enhancing components, absorbent components, or gelling compounds, will reduce the osmotic pressure correspondingly. In addition, these patents were written prior to the introduction of the concept that MMPs are responsible for wound chronicity.

Accordingly, a need exists for a composition that allows the effective application of polysaccharides in high concentrations to a wound surface. A need also exists to for a composition that provides non-sharp debridement while also controlling the level of MMPs present in the wound.

SUMMARY OF THE INVENTION

In order to address the shortcomings of the prior art and in accordance with the present invention, a technology is described that allows the combination of solid and liquid polysaccharides, and the application of such combinations on absorbent substrates in a way that is anisotropic. Specifically, the application technology allows, at least transiently, a higher concentration of total sugars on the one surface of the wound, preferably the wound contacting surface of the dressing compared to the non wound contacting surface of the dressing.

The present invention also includes embodiments that provide non-sharp debridement of a wound while also controlling the level of MMPs present in the wound. Such debridement can be accomplished by the use of honey as a part of a wound-healing package. Honey debrides via osmotic pressure, and its acidity that is well known tends to denature, at least temporarily, MMPs that lead to wound chronicity.

Embodiments of the invention include a dressing for application to a wound that includes a wound contacting layer for contacting the wound surface. The wound contacting layer is made up of a mixture of a first polysaccharide with a first viscosity and a second polysaccharide. The second polysaccharide may be a liquid or gel with a greater viscosity or a solid. The first and second polysaccharides are mixed together so that the wound contacting layer has a viscosity that is between the individual viscosities of the two polysaccharides. In embodiments of the invention, the first polysaccharide is honey and the second polysaccharide is cane sugar.

BRIEF DESCRIPTION OF THE DRAWINGS

The foregoing and other advantages of the invention will become apparent upon reading the following detailed description and upon reference to the drawings.

Figure 1:
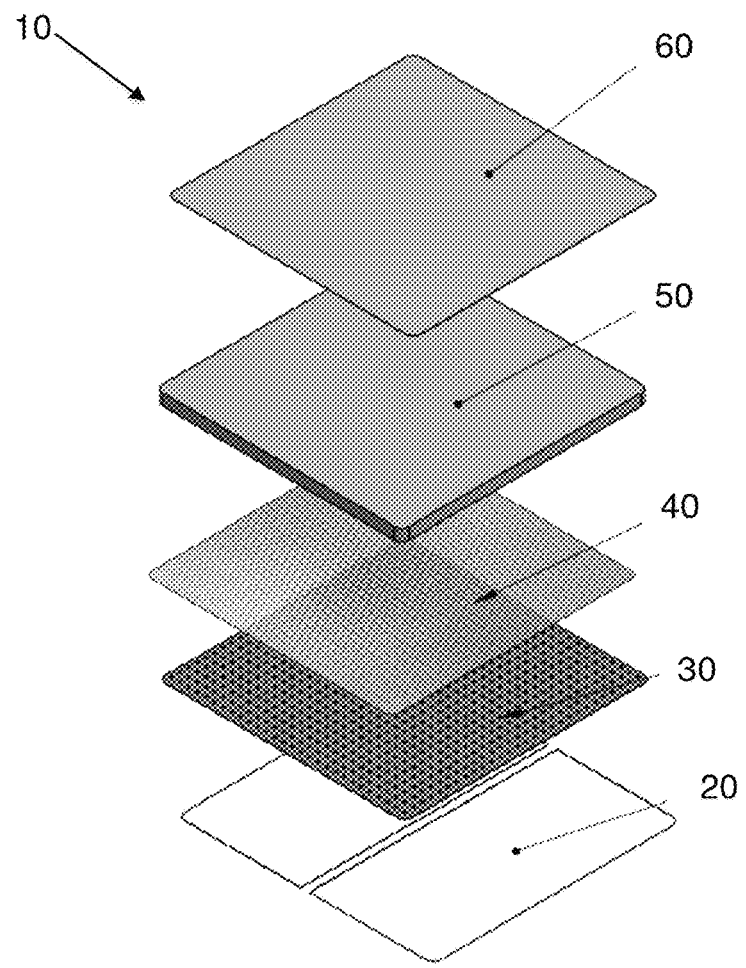
FIG. 1 is an exploded view of a wound dressing having various layers according to one embodiment of the invention.
Figure 2:
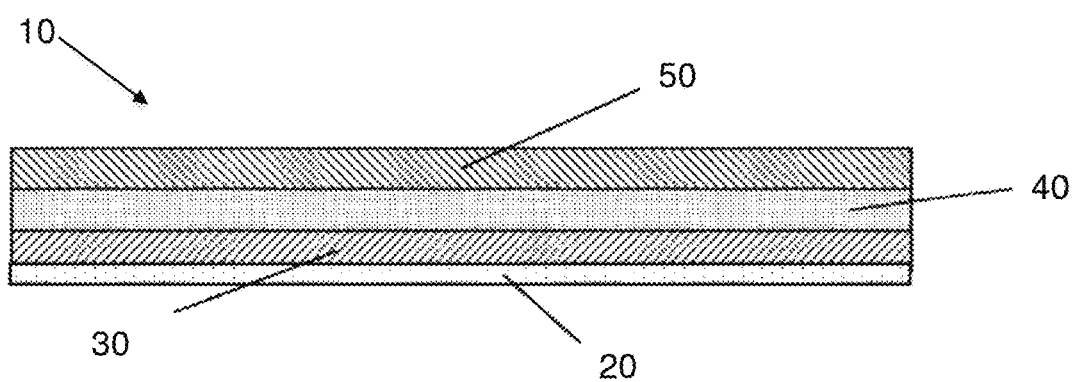
FIG. 2 is cut-away, side view of a wound dressing having various layers according to one embodiment of the invention.

The view of FIGS. 1 and 2 are intended to illustrate the composition of a wound dressing in accordance with embodiments of the present invention. The views are not to scale and are not intended to limit the dimensions or structure of the invention. While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions Embodiments of the present invention perform the objective of having a high sugar concentration when a dressing is presented to the wound but still satisfying practical considerations such as adhesion of the sugar or sugar mix onto an appropriate surface. Embodiments of the present invention include the use of substrates that are absorbent, or microcellular, yet that do not allow the ingress of the sugars into the substrate to such as extent that the substrate material is present at the primary wound contact layer as a diluent to the polysaccharide elements. Accordingly, embodiments of the present invention reduce the percentage of non-polysaccharide material coming in contact with the polysaccharide in the first layer of the dressing that is applied to the wound.

In embodiments of the invention, two types of sugars are mixed in variable proportions, so that the optimum viscosity of the sugar mixture is somewhere between a liquid polysaccharide, such as honey, and a solid polysaccharide, such as cane sugar. This composition can be laminated to substrates of various types, for example, polyurethane foams, or super absorbent polymer films or papers. The use of such substrates may allow additional convenience in delivering the active agent. The active agent, honey plus cane sugar, can be laminated to a substrate. For example, a highly viscous mixture of cane sugar and honey can be created by mixing the sugars in a sigma mixer. The mixture can then be extruded by a screw type extruder, or any other appropriate means, onto the substrate. The substrate is chosen so that it does not allow easy immediate ingress of the entire sugar mixture into the substrate.

FIGS. 1 and 2 illustrate an embodiment of the present invention. As shown, a dressing 10 in accordance with the present invention may include a backing layer 20. The backing layer provides protection for the dressing during manufacture and transportation and is removed prior to applying the dressing to a wound. The backing layer may be a laminated paper or another protective layer as would be apparent to one of ordinary skill in the art.

The dressing 10 may also include a polysaccharide layer 30. Embodiments of the polysaccharide layer 30 include various compositions of a first fluid polysaccharide material combined with a second polysaccharide material. The second polysaccharide material may be a fluid having a greater viscosity than the first fluid, or it may be a solid material. The fluid polysaccharide material may be honey, and more specifically Manuka honey. The second polysaccharide material may be sugar, and in particular, cane sugar or its byproducts. For purposes of the invention, cane sugar includes equivalent sugar obtained from other sources, for example, sugar derived from sugar beets. The sugar may be of various forms including crystalline sugar, powdered sugar, or syrup.

The ratio of the polysaccharide components in the polysaccharide layer may vary depending upon the desired viscosity of the layer. It is contemplated that the ratio of first and second polysaccharides may be varied such that the resulting polysaccharide layer forms a solid, a liquid, a gel or a free-flowing particulate material. In particular, embodiments of the a polysaccharide layer for use in the present invention may include less than 50% by weight of honey and more than 50% by weight of solid cane sugar. For example, the polysaccharide layer may include between 5% and 45% by weight of honey and between 55% and 95% by weight of solid cane sugar. The resulting polysaccharide layer may be composed of a solid, a liquid, a gel or a free-flowing particulate material.

Alternatively, the polysaccharide layer 30 may comprise two or more layers of polysaccharide material having the same or different compositions. For example, the polysaccharide layer may have a first layer adjacent to the wound surface that contains only honey and cane sugar in order to stimulate debridement of the wound. The polysaccharide layer may then include a second layer that contains honey, cane sugar and additional materials. These additional materials may include materials having antibiotic effects, such as silver or silver compounds. Other materials having known tissue health promoting properties may also be included. For example, the second layer may include collagen, such that the layer including collagen, which provides for additional suppression of MMPs is exposed to the wound only after the first layer has dissolved.

As shown in FIGS. 1 and 2, the dressing 10 may also include a film layer 40. The film layer may comprise a polymer film, paper, a woven or non-woven fabric, or the like. The film layer may also include through apertures that allow fluid from the wound to pass through the film layer. The polysaccharide layer 30 may be extruded onto, adhered to, laminated to, or encapsulate the film layer 40.

The dressing may also include an absorbent layer 50. The absorbent layer may be composed of polyurethane foam, cellulose fiber or another appropriate absorbent material. The absorbent layer 50 may be adhered or laminated to the film layer 40. Alternatively, the film layer may be dispensed with, and the polysaccharide layer 30 may be applied directly to the absorbent layer. Whether the polysaccharide layer 30 is applied to a film layer 40 or directly an absorbent layer 50, the substrate is chosen so that it does not allow easy immediate ingress of the entire sugar mixture into the substrate.

As shown in FIG. 1, the dressing may also include a cover layer 60. The cover layer may polymer film such as a polyurethane film. Alternatively the cover layer may be a woven or non-woven fabric or another appropriate covering material. The cover material may be fluid impervious in order to contain fluid absorbed by the dressing from the wound. The cover material may also be a breathable material.

FIGS. 1 and 2 illustrate the various layers as being coterminous. However, the layers may extend past one another. For example, the cover layer 60 shown in FIG. 1 may extend beyond the periphery of the polysaccharide layer 30. A skin facing surface of the cover layer may be adhesive such that the cover layer serves to adhere to dressing to the patient's skin.

What is claimed is:

1. A dressing for application to a wound comprising:
a cover layer;
an absorbent layer;
a first polysaccharide layer consisting of: honey and solid cane sugar; and
a second polysaccharide layer comprising: honey, cane sugar and an additional material;
wherein the honey and cane sugar of the first polysaccharide layer form a mixture in the first polysaccharide layer having a first viscosity that is greater than the viscosity of the honey.

2. The dressing of claim 1, wherein the first polysaccharide layer is less than 50% by weight of honey.

3. The dressing of claim 1, wherein the first polysaccharide layer is more than 50% by weight of cane sugar.

4. The dressing of claim 1, wherein the additional material of the second polysaccharide layer is a material having tissue health promoting properties.

5. The dressing of claim 1, wherein the additional material of the second polysaccharide layer is a material having antibacterial properties.

6. The dressing of claim 1 wherein the honey, cane sugar and additional material of the second polysaccharide layer form a mixture in the wound contacting layer having a second viscosity that is different from the viscosity of the wound contacting layer.

7. The dressing of claim 2, wherein the first polysaccharide layer is between 10% and 45% by weight of honey.

8. The dressing of claim 3, wherein the first polysaccharide layer is between 55% and 90% by weight of cane sugar.

9. The dressing of claim 2, wherein the first polysaccharide layer is more than 45% and less than 50% by weight of honey.

10. The dressing of claim 1 further comprising:
a film layer,
wherein the second polysaccharide layer is applied to the film layer.

* * * * *